United States Patent
Droescher et al.

(10) Patent No.: US 6,172,056 B1
(45) Date of Patent: Jan. 9, 2001

(54) PHARMACEUTICAL COMPOSITIONS AND METHOD FOR PROPHYLAXIS AND THERAPY OF RADICAL-MEDIATED CELL DAMAGE

(75) Inventors: Peter Droescher, Weimar; Bernd Menzenbach, Jena; Kurt Ponsold, Jena; Bernd Undeutsch, Jena; Michael Oettel, Jena; Wolfgang Römer, Jena; Günter Kaufmann, Jena; Jens Schroeder, Jena, all of (DE)

(73) Assignee: Jenapharm GmbH & Co. KG, Jena (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/646,341

(22) PCT Filed: Nov. 8, 1994

(86) PCT No.: PCT/DE94/01309

§ 371 Date: May 9, 1996

§ 102(e) Date: May 9, 1996

(87) PCT Pub. No.: WO95/13076

PCT Pub. Date: May 18, 1995

(30) Foreign Application Priority Data

Nov. 10, 1993 (DE) .................................................. 43 38 314

(51) Int. Cl.[7] .................................................. A61K 31/56
(52) U.S. Cl. .................................................. 514/182; 514/173
(58) Field of Search ..................................... 552/618, 500, 552/510, 602, 617, 625; 540/46; 514/173, 182

(56) References Cited

U.S. PATENT DOCUMENTS

| | | | |
|---|---|---|---|
| 3,436,411 | * | 4/1969 | Stein et al. ............................ 552/618 |
| 4,897,389 | | 1/1990 | Aroonsakul . |
| 5,405,944 | * | 4/1995 | Suzuki ..................................... 536/5 |
| 5,554,601 | | 9/1996 | Simpkins et al. . |

FOREIGN PATENT DOCUMENTS

| | | |
|---|---|---|
| 0389370 | 3/1990 | (EP) . |
| 0389368 | 9/1990 | (EP) . |
| 2640977 | 12/1988 | (FR) . |
| WO87/01706 | 3/1987 | (WO) . |
| WO91/11453 | 8/1991 | (WO) . |

OTHER PUBLICATIONS

WPIDS AN 93–110917, Ishida et al., 1993.*
WPNDS AN 96–041521, Ishida et al., 1992.*
CAS119:109303, Mooradian, J. Ster. Biochem. Mol. Biol., 1993.*
CA121:179977, Jun. 1, 1994.*
CA 108: 198542, Gyhing et al, J Ster. Bioch., 1988.*
CA 105:219024, Barth et al, Arch. Int. Pharmacodyn. Ther, 1986.*
A. Mooradian "Antioxidants Properties of Steroids", J. Steroid. Biochem. Molec. Biol., vol. 45, No. 6, pp. 509–511 (1993).
H. Esterbauer, et al "Effect of Peroxidative Conditions of Human Plasma Low–Density Lipoproteins", Eicosanoids, Lipid Peroxidation and Cancer, S.K. Nigam, D.C. H. McBrien, eds., Springer–Veriag, pp. 203–213.
J. Phys. Org. Chem. Inhibition of Peroxidatons of Lipids and Membranes by Estro_Gens. Komuro, et al., vol. 3, 309–315, 1990.
Eicosanoids, Lipid Peroxidation and Cancer; Nigam, et al., 1988, pp. 203–213.

* cited by examiner

Primary Examiner—Rebecca Cook
(74) Attorney, Agent, or Firm—Michael J. Striker

(57) ABSTRACT

The method of prophylaxis and therapy of radical-mediated cell damage includes administering an effective amount of at least one steroid and at least one pharmaceutical adjuvant to a human being. The at least one steroid is selected from the group consisting of ent-estradiol, 17α-estradiol, 8-dehydroestradiol, 8-dehydro-17α-estradiol, 8(14)-dehydroestradiol, 6,8-didehydro-17α-estradiol, 6-dehydroestriol, 9(11)-dehydroestriol, 20-hydroxymethyl-3-hydroxy-19-norpregna-1,3,5(10)-triene, 14α, 15α-methylene-8-dehydroestradiol, 14α, 15α-methylene-estradiol, 2-hydroxy-estradiol-3-methyl ether, 3-hydroxy-1,3,5(10)-estratriene-17S-spirooxirane, 3-hydroxy-1,3,5(10),9(11)-estratetraene-17S-spirooxirane, and 14β,15β-methylene-8-dehydroestradiol. This method strongly inhibits changes in cells and tissues, such as lipid peroxidation and oxidation of low-density lipoprotein (LDL) cholesterol, triggered by reaction oxygen species, free oxygen radicals and other forms of radicals and thus reduces attendant irreversible membrane and endothelial damage.

8 Claims, No Drawings

PHARMACEUTICAL COMPOSITIONS AND METHOD FOR PROPHYLAXIS AND THERAPY OF RADICAL-MEDIATED CELL DAMAGE

This application is a 371 of PCT/DE94/01309 filed Nov. 8, 1994.

BACKGROUND OF THE INVENTION

The invention relates to novel pharamaceutical preparations for prophylaxis and therapy of radical-mediated cell damage.

From professional and patent literature it is known that reactive oxygen species (ROSs), free oxygen radicals and other radial forms play an important role in the occurrence of many kinds of cell damage, such as ischemic and traumatic organ injuries, and inflammatory and toxic processes.

A negative effect of ROSs, free oxygen radicals and other forms of radicals can also be found in brain and spinal column injuries, shock states, stroke, muscular dystrophy, emphysemas, adult respiratory distress syndrome (ARDS), asthma, aging processes, in tissue damage after myocardial infarction, damage from toxic processes and radiation, burns, and transplant-dictated immune reactions. Among other factors, lipid peroxidation and the oxidation of low-density lipoprotein (LDL) cholesterol, combined with irreversible membrane and endothelial damage are the starting point for such radical-mediated cell damage.

It is also known that lipophilic substances, such as lipophilic steroids, with "radical-trapping" properties can be suitable for prophylaxis and therapy of radical-mediated cell damage.

Unlike the known low-molecular phenolic antioxidants, these lipophilic steroids are transported with a certain selectivity into the region of the cell membrane or endothilium, where they can develop their efficacy.

The therapeutic utility is determined by the action spectrum of the respective substance.

International Patents WO 87/01716 and WO 91/11453, European Patents EP 0 389 368, EP 0 389 369, and EP 0 389 370, and French Patent FR 2 640 977, for instance, describe steroids with "radical-trapping" properties.

WO 87/01716, WO 91/11453 and EP 0 389 368/... 369/... 370 describe steroids describe steroids which contain an amino group, which can be substituted or part of a heterocyclic ring system, this amino group being bonded to the terminal carbon atom of a side chain at the $C_{17}$ position of the steroid.

In FR 2 640 977, a structural type is shown that has a substituted phenyl ring in the $\beta$ position on the $C_{11}$ atom.

It is shown in J. Phys. Org. Chem. 3 (1990), 309–315 that estrogens, and especially catechol estrogens, can act as radical catchers. Estradiol, estrone, estriol and 2-hydroxyestradiol inhibit peroxidation in vitro and in vivo.

SUMMARY OF THE INVENTION

The object of the invention is to discover novel pharmaceutical preparations with high efficacy for prophylaxis and therapy of radical-mediated cell damage.

According to this invention, this object is attained in that pharmaceutical preparations have been discovered that comprise steroids with a phenolic A-ring structure, except for the estrogens whose action in this respect is known, that is, 17β-estradiol, estrone, estriol and their 2-hydroxy derivatives, steroids with cyclic substituents or with an amino group at the terminal C atom of the aliphatic $C_{17}$ side chain, and that also comprise pharmaceutical adjuvants.

In a preferred embodiment of the invention these pharmaceutical compositions include at least one additional conjugated double bond, which is advantageously an 8(14) double bond.

In various embodiments of the invention the at least one steroid active ingredient is ent-estradiol, 17α-estradiol, 8-dehydroestradiol, 8-dehydro-17α-estradiol, 8(14)-dehydroestradiol, 6,8-didehydro-17α-estradiol, 6-dehydroestriol, 9(11)-dehydroestriol, 20-hydroxymethyl-3-hydroxy-19-norpregna-1,3,5(10)-triene, 14α,15α-methylene-8-dehydro-estradiol, 14α, 15α-methylene-estradiol, 2-hydroxy-estradiol-3-methyl ether, 3-hydroxy-1,3,5(10)-estratriene-17S-spirooxirane, 3-hydroxy-1,3,5(10),9(11)-estratetraene-17S-spirooxirane and 14β,15β-methylene-8-dehydroestradiol.

The pharmaceutical preparations for oral and parenteral, including topical, rectal, subcutaneous, intravenous, intramuscular, intraperitoneal, intranasal, intravaginal, intrabuccal or sublingual adminstration in addition to typical vehicles and diluents contain one of the above-described steroid compounds according to the invention as active ingredient.

The medications of the invention are prepared in a known manner with the usual solid or liquid vehicles or diluents and with the typically used pharmaceutical-technical adjuvants, depending on the desired type of application and with suitable dosing.

The advantages of the invention are attained substantially because novel pharmaceutical preparations for prophylaxis and therapy of radical-mediated cell damage have been discovered, having active ingredients whose action profile differs from the known estrogens mentioned above and from that of vitamin E, and/or having active ingredients which have high efficacy with regard to the inhibition of lipid peroxidation and LDL oxidation in vitro, in comparison to the aforementioned estrogens, to U-78517F, and to vitamin E.

The advantageous action of the systems according to the invention as inhibitors of lipid peroxidation and LDL oxidation are demonstrated in Table 1 and Table 2.

As comparisons to the systems of the invention, 17β-estradiol, estriol, U-78517F and vitamin E are likewise shown, marked (x), in Table 1 and Table 2.

The measurement of the in vitro inhibition of lipid peroxidation was done by means of the thiobarbituric acid test. The lipid peroxidation-inhibiting action of the respective compound is characterized with the statement of the $IC_{50}$ inhibition values. $IC_{50}$ indicates the quantity of substance to be added in order to attain a 50% inhibition of lipid peroxidation (Table 1). The measurement of in vitro inhibition of LDL oxidation was performed in accordance with Esterbauer et al (1988): Effect of peroxidative conditions on human plasma low density lipoproteins. In: Eicosanoids, lipid peroxidation and cancer (ed. Nigam et al), pages 203–214, Springer-Verlag, Berlin, Heidelberg, New York.

The values listed in Table 2 for inhibition of LDL oxidation represent examples for cardiovascular activities.

Statements about estrogen affinity are made by measuring the estrogen receptor binding.

Measuring the estrogen receptor binding is done by competitive binding of the $^3$H-labelled synthetic estrogen ethinyl estradiol and of the compounds to be tested in uterine cytosol of the infantile rabbit at 0° C. Reaction equilibrium and receptor saturation are the goal.

From series of concentrations that include the last $IC_{50}$ values, the $IC_{50}$ for the standard substance 17β-estradiol and for the compound to be tested are ascertained (regression calculation by logit-log transformation), and the relative binding affinity (RBA) is indicated as the quotient of these two values.

With the statement about the RBA values, the estrogen receptor affinity of the particular compound is characterized; taking into account certain prerequisites for in vitro investigations (such as a free 30H group), it is a measure for estrogen affinity (again, see Table 1).

TABLE 1

Lipid peroxidation inhibition and estrogen receptor affinity of selected compounds

| Compound | Lipid peroxidation inhibition $IC_{50}$;μmol) | Relative binding affinity to estrogen receptor (%) |
|---|---|---|
| 17β-Estradiol (x) | 12.4 | 100 |
| ent-Estradiol | 8.8 | 6.7 |
| 17α-Estradiol | 8.9 | 22.8 |
| 8-Dehydroestradiol | 1.0 | 59.6 |
| 8-Dehydro-17α-estradiol | 4.1 | |
| 8(14)-Dehydroestradiol | | |
| 6,8-Didehydro-17α-estradiol | 5.1 | |
| Estriol (x) | 122.5 | 10.3 |
| 6-Dehydroestriol | 45.6 | 7.9 |
| 9(11)-dehydroestriol | 10.6 | 7.5 |
| 20-hydroxymethyl-3-hydroxy-19-norpregna-1,3,5(10)-triene | 14.4 | 22.5 |
| Vitamin E (x) | 132 | |
| U-78517F (x) | 1.8 | |
| 14α,15α-Methylene-8-dehydroestradiol | 0.9 | |
| 14α,15α-Methylene estradiol | 5–10 | |
| 14β,15β-Methylene-8 dehydroestradiol | 1.9 | |
| 2-Hydroxyestradiol-3-methyl ether | 3.2 | |
| 3-Hydroxy-1,3,5(10)-estratetraene-17S-spirooxirane | 4.11 | |
| 3-hydroxy-1,3,5(10),9(11)-estratetraene-17S-spirooxirane | 0.81 | |

TABLE 2

LDL oxidation inhibitions of selected compounds (5 μmol)

| Compound | LDL oxidation inhibition (prolongation of the lag phase in min) |
|---|---|
| 17β-Estradiol (x) | 110 |
| ent-Estradiol | 120 |
| 8-Dehydroestradiol | 120 |
| Estriol (x) | 45 |
| U-78517F (x) | 70 |
| 3-Hydroxy-1,3,5(10)-estratriene-17S-spirooxirane | 170 |
| 3-Hydroxy-1,3,5(10),9(11)-estratetraene-17S-spirooxirane | 210 |

It can be seen from Table 1 that the radical scavenger properties are independent of the estrogen affinity of the various compounds. For example, the in vitro inhibition on lipid peroxidation for ent-estradiol is just as high as for 17α-estradiol, but the estrogen affinity is significantly different.

It can also be seen from Table 1 and Table 2 that the compounds ascertained according to the invention have both a lipid peroxidation-inhibiting and a LDL oxidation-inhibiting action in vitro, which is higher than that of vitamin E or is on the order of magnitude of or better than that of 17βestradiol, estriol, and U-78517F.

It has also been discovered that conjugated double bonds, such as the 6-, 8- and 9(11)-double bond, like the 8(14)-double bond, lead to a considerable increase in lipid peroxidation and LDL oxidation inhibition.

The preparations according to the invention represent both inhibitors of lipid peroxidation and inhibitors of LDL oxidation and are therefore suitable for prophylaxis and therapy of radical-mediated cell damage, such as in the case of spinal trauma, ischemic (thromboembolytic) stroke, ischemia, organ damage in the re-perfusion phase after transplants, chronic-degenerative CNS diseases, senile dementia of the Alzheimer's type (SDAT), asthma, muscular dystrophy, and degenerative neurological diseases, including those in the form of toxic or degenerative CNS states.

The preparations according to the invention likewise prove to be advantageous for prophylaxis and therapy of such diseases, caused by radical-mediated cell damage, as multiple sclerosis, skin graft reaction, acute pancreatitis, liver necroses (such as viral hepatitis), hemorrhagic, traumatic and septic shock, inflammatory states such as osteo- or rheumatoid arthritis, adjuvant arthritis, arthrosis, nephrotic (immunological) syndrome, systemic lupus erythematosis, adriamycin-induced heart toxicity, and neuroprotective brain tumors.

The preparations according to the invention are also suitable for prophylaxis and therapy of such diseases, caused by radical-mediated cell damage, as allergic reactions, atherosclerosis, inflammation under dermatological, inflammatory and psoriatic conditions, stress-induced ulcer, migraine, malignant hyperthermia, hypoxia syndrome, ischemic bowel syndrome, and the reduction of the necessary dose in the therapeutic application of radical-degrading enzymes, such as superoxide dismutase and catalase.

The medications according to the invention are also usable as antitumor active ingredients and are suitable for the prophylactic and therapeutic treatment of cardiac and circulatory disease states.

Investigations of the pharmacological efficacy of the "radical-trapping" substances Testing of the substances for inhibitory effect with regard to lipid peroxidation was carried out as follows, using the thiobarbituric acid test:

Reaction mixture 1 ml of biological specimen (containing 0.1 mg of plasma membranes), including Fenton's reagent and test substance.

The total volume of 1 ml is divided into 0.01 to 0.02 ml synaptosomal membrane fraction; 0.1 ml iron (II) chloride (2 mmol); 0.1 ml hydrogen peroxide (2 mmol), replenish to 1 ml with 0.9% NaCl (not PBS) and ethanol or DMSO as a vehicle for the test substance.

Procedure

The reaction mixture is incubated for 30 min at 37° C., then stopped with 2 ml of reagent A and incubated for 10 min at a constant 80° C. After cooling down in an ice bath (10 min), the specimen is centrifuged in a cooling centrifuge (1000×g; 4° C.). The residue (stable for up to 2 h) is measured at 535 nm against the blind value, which except for the membrane fraction contains all the reagents.

As a comparison value, the mixture is used that contains, besides the membrane fraction, NaCl and in a given case vehicle with the same proportions.

Composition of reagent A

15% (w/v) trichloroacetic acid (15 g); 0.375% (w/v) thiobarbituric acid (375 mg); 0.25 n HCl (2.11 ml of concentrated HCl)

in 100 ml of aqueous solution.

Test substances

The test substances are preferably mixed in ethanol as 20 millimolar parent solutions and diluted accordingly. The dosage range from 1 to 150 μmol was tested.

A suitable standard substance is included in all the test kits.

Evaluation parameters

Dosage-action analysis of the test substances.

Ascertainment of the lipid peroxidation inhibition values with at least five substance concentrations in the inhibition range from 30 to 70%, referred to the test values without substance effect.

Testing of the substances for inhibitory action with regard to LDL oxidation, by the method of Esterbauer et al (1988), was carried out as follows:

Reaction mixture 2 ml of biological specimen (containing 0.5 mg LDL, isolated from human whole blood, including 10 μmol $CuSO_4$ and from 1 to 150 μmol of test substance and ethanol as a vehicle for the test substance in the cell-free medium PBS.

Procedure

The reaction mixture is incubated at room temperature over a period of at least 8 h and followed spectral photometrically (the absorption maximum of the oxidized LDL is at 234 nm). In accordance with the extinction changes, recorded at the measurement wavelength of 234 nm, in the presence or absence of test substances or in comparison of the native and the oxidized LDL, definitive statements on the influence on the oxidized LDL by the action of the test substance.

Test substances

The test substances are preferably mixed in ethanol as 20 millimolar parent solutions and diluted accordingly. The dosage range from 1 to 150 μmol was tested.

A suitable standard substance is included in all the test kits.

Evaluation parameters

Dosage-action analysis of the test substances.

Ascertainment of the LDL oxidation inhibition values, demonstrated as a delay in LDL oxidation in the form of a chronologically prolonged lag period (in min).

We claim:

1. A method of prophylaxis and therapy of radical-mediated cell damage, in a human being in need thereof said method comprising administering an effective amount of at least one steroid and at least one pharmaceutical adjuvant to a said human being, wherein said at least one steroid is selected from the group consisting of ent-estradiol, 8-dehydro-estradiol, 8-dehydro-17α-estradiol, 8(14)-dehydro-estradiol, 6,8-didehydro-17α-estradiol, 6-dehydroestriol, 9(11)-dehydroestriol, 20-hydroxymethyl-3-hydroxy-19-norpregna-1,3,5(10)-triene, 14α, 15α-methylene-8-dehydroestradiol, 14α, 15α-methylene-estradiol, 2-hydroxy-estradiol-3-methyl ether, 3-hydroxy-1,3,5(10)-estratriene-17S-spirooxirane, 3-hydroxy-1,3,5(10), 9(11)-estratetraene-17S-spirooxirane and 14β, 15βB-methylene-8-dehydroestradiol.

2. A method of prophylaxis and therapy of, radical-mediated cell damage in a human being in need thereof said method comprising administering an effective amount of 14α, 15α-methylene-8-dehydroestradiol and at least one pharmaceutical adjuvant to said human being.

3. The method as defined in claim 1, wherein said at least one pharmaceutical adjuvant is water, ethanol or a mixture therof.

4. A method of prophylaxis and therapy of radical-mediated cell damage in a human being in need thereof, said method comprising administering an effective amount of 14β,15β-methylene-8-dehydroestradiol and at least one pharmaceutical adjuvant to said human being.

5. A method of inhibiting lipid peroxidation and low density lipoprotein (LDL) oxidation in a human being in need thereof LDL oxidation, said method comprising administering to said human being an effective amount of at one steriod selected from the group consisting of ent-estradiol, 8-dehydro-estradiol, 8-dehydro-17α-estradiol, 8(14)-dehydro-estradiol, 6,8-didehydro-17α-estradiol, 6-dehydroestriol, 9(11)-dehydroestriol, 20-hydroxymethyl-3-hydroxy-19-norpregna-1,3,5(10)-triene, 14α,15α-methylene-8-dehydroestradiol, 14α, 15α-methylene-estradiol, 2-hydroxy-estradiol-3-methyl ether, 3-hydroxy-1,3,5(10)-estratriene-17S-spirooxirane, 3-hydroxy-1,3,5(10), 9( 11)- estratetraene-17S-spirooxirane and 14β, 15β-methylene-8-dehydroestradiol.

6. A method of inhibiting lipid peroxidation and low density lipoprotein oxidation in a human being in need thereof, said method comprising administering an effective amount of 14α, 15α-methylene-8-dehydro-estradiol to said human being.

7. A method of inhibiting lipid peroxidation in a human being in need thereof, said method comprising administering to said human being at least one pharmaceutical adjuvant together with an effective amount of at least one steroid selected from the group consisting of ent-estradiol, 8-dehydroestradiol, 8-dehydro-17α-estradiol, 8(14)-dehydro-estradiol, 6,8-didehydro-17α-estradiol, 6-dehydroestriol, 9(11)-dehydroestriol, 20-hydroxymethyl-3-hydroxy-19-nor-pregna-1,3,5(10)-triene, 14α, 15α-methylene-8-dehydro-estradiol, 14α, 15α-methylene-estradiol, 2-hydroxy-estradiol-3-methyl ether, 3-hydroxy-1,3,5(10)-estratriene-17S-spiro-oxirane, 3-hydroxy-1,3,5(10), 9(11)-estratetraene-17S-spiro-oxirane and 14β, 15βB-methylene-8-dehydro-estradiol.

8. A method of inhibiting low density lipoprotein oxidation in a human being in need thereof, said method comprising administering to said human being at least one pharmaceutical adjuvant together with an effective amount of at least one spiroxirane compound selected from the group consisting of 3-hydroxy-1,3,5(10 )-estratriene-17S-spirooxirane and 3-hydroxy-1,3,5(10),9(1)-estratetraene-17S-spirooxirane.

* * * * *